United States Patent
Zinaty et al.

(10) Patent No.: US 8,467,603 B2
(45) Date of Patent: Jun. 18, 2013

(54) METHOD FOR ENHANCING IN-VIVO IMAGE CONTRAST

(75) Inventors: Ofra Zinaty, Haifa (IL); Igor Zingman, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 1141 days.

(21) Appl. No.: 12/393,407

(22) Filed: Feb. 26, 2009

(65) Prior Publication Data
US 2009/0214111 A1 Aug. 27, 2009

Related U.S. Application Data
(60) Provisional application No. 61/021,696, filed on Feb. 26, 2008.

(51) Int. Cl.
*G06K 9/00* (2006.01)
(52) U.S. Cl.
USPC .......................................................... 382/167
(58) Field of Classification Search
USPC ................. 382/162, 167, 239, 274; 600/109
See application file for complete search history.

(56) References Cited

U.S. PATENT DOCUMENTS

| | | | |
|---|---|---|---|
| 5,604,531 | A | 2/1997 | Iddan et al. |
| 5,883,984 | A | 3/1999 | Huang et al. |
| 7,009,634 | B2 | 3/2006 | Iddan et al. |
| 7,428,332 | B2 | 9/2008 | Spaulding et al. |
| 2003/0117654 | A1 | 6/2003 | Wredenhagen et al. |

FOREIGN PATENT DOCUMENTS

| | | |
|---|---|---|
| EP | 1 206 123 | 5/2002 |
| EP | 1383341 | 1/2004 |
| GB | 2352354 | 1/2001 |

OTHER PUBLICATIONS

Office Action for European Patent Application No. 09 002 747.5 dated May 2, 2011.
Yeong-Taeg et al., "Contrast Enhancement Using Brightness Preserving Bi-Histogram Equalization", IEEE Transactions on Consumer Electronics, vol. 43, No. 1, pp. 1-8, Feb. 1, 1197.
European Search Report for European Application No. EP 09002747, mailed on Mar. 23, 2010.

*Primary Examiner* — Duy M Dang
(74) *Attorney, Agent, or Firm* — Pearl Cohen Zedek Latzer, LLP

(57) ABSTRACT

This invention relates to methods for enhancing an image by expanding the color contrast of the image presented to a wider range of colors that is optimized for the item sought to be viewed. The method also increases contrast of an image or a portion of an image for example an in vivo image captured by an autonomous in vivo device. A user interface with a display provides the user with the option of viewing selected images captured by the in-vivo imaging device in either regular view or in a color enhanced view to enable more distinct viewing of the selected images.

14 Claims, 5 Drawing Sheets
(3 of 5 Drawing Sheet(s) Filed in Color)

METHOD FOR ENHANCING IN-VIVO IMAGE CONTRAST

CROSS-REFERENCE TO RELATED APPLICATIONS

This application claims priority from U.S. Provisional Patent Application No. 61/021,696, filed Jan. 17, 2008, which is hereby incorporated by reference.

FIELD OF INVENTION

The present invention relates to an in-vivo device and method such as for imaging an in-vivo lumen. More specifically, the present invention relates to a method and apparatus in an in-vivo system for presenting in-vivo data viewed by an autonomous in-vivo imaging device.

BACKGROUND OF THE INVENTION

Known devices may be helpful in providing in-vivo sensing, such as imaging or pH sensing. Autonomous in-vivo sensing devices, such as swallowable or ingestible capsules or other devices, may move through a body lumen, sensing as they move along. An autonomous in-vivo sensing device such as an imaging device may include, for example, an imager for obtaining images from inside a body cavity or lumen, such as the gastrointestinal (GI) tract while the in-vivo imaging device passes through the GI lumen. The imager may, for example, be associated with an optical system, and optionally a transmitter and an antenna. Some of these devices use a wireless connection to transmit image data. Other devices, systems and methods for in-vivo sensing of passages or cavities within a body, and for sensing and gathering information (e.g., image information, pH information, temperature information, electrical impedance information, pressure information, etc.), are known in the art.

Viewing pathologies such as tumors, lesions or ulcers and the like may be complicated by the fact that the gastrointestinal tract and the item or pathology sought to be viewed have very similar background color.

Different methods exist for enhancing in vivo image contrast. One method is to render grayscale digital images in pseudocolor by assigning specific gray level ranges to particular color values. This technique is useful for highlighting particular regions of interest in grayscale images because the human eye is better able to discriminate between different shades of color than between varying shades of gray. Pseudocolor imaging is widely employed in fluorescence microscopy to display merged monochrome images obtained at different wavelengths utilizing multiply stained specimens. Often, the color assigned to individual fluorophore images in a collage assembly is close in color to that naturally emitted by the fluorescent dye.

Another technique for enhancement of vascular images is narrow-band imaging (NBI), which is an optical filter technology that improves the visibility of subtle tissue structures based upon the phenomenon that the depth of light penetration depends on its wavelength (shorter wavelength light, e.g., blue, penetrates only superficially, whereas longer wavelength light, e.g., red, penetrates into deeper layers). In one NBI system, white light is passed through a rotary red-green-blue filter to sequentially illuminate a mucosa with RGB illumination, and the reflected light is detected separately and integrated into a single color image by a video processor. In another NBI system, two discrete bands of light, one blue at 415 nm, and one green at 540 nm, are used. Narrow band blue light displays superficial capillary networks, while green light displays subepithelial vessels, and when combined they offer an extremely high contrast image of the tissue surface. For example, in an NBI image on a monitor, capilaries on the surface can be displayed in brown, and veins in the sub surface can be displayed in cyan.

In addition, FUJI Intelligent Color Enhancement (FICE), developed by Fujinon, Inc. of New Jersey, a wholly owned subsidiary of Fujinon Corporation of Saitama City, Japan, provides endoscopic diagnosis systems based on spectral estimation technology. In this system, a processor takes ordinary endoscopic images from the video processor and arithmetically processes, estimates and produces an image of a given, dedicated wavelength of light so as to enable clearer observation of tissue characterization on surface parts and of capillary orientations.

SUMMARY OF THE INVENTION

The present invention relates in one embodiment to presentations of in-vivo data viewed by an autonomous in-vivo imaging device and introduces a method of enhancing the color contrast of images generated in vivo. According to some embodiments, this method may be used to complement known methods in the art. According to some embodiments, this method may be used to enhance other types of images which are not in-vivo images, for example images that have a mostly uniform shade or tint, such as an image of a foggy street, which may be mostly bluish-gray, or landscape images of meadows which may be mostly greenish. According to some embodiments, this method may be used for making indistinct objects or features in images more prominent by enhancing the image color contrast. The enhanced colors in the image may or may not bear resemblance with their natural hues.

Some embodiments of the present invention may provide methods for generating and displaying a fixed graphical presentation of captured in-vivo data streams having enhanced color contrast.

In one embodiment, described herein are methods for enhancing the image obtained by an autonomous in-vivo imaging device, by expanding or stretching the pixel color characteristics, and present an enhanced image that highlights the items sought to be viewed, or is optimized for the items sought to be viewed.

In another embodiment of the present invention, provided herein is a computer-implemented method for constructing a color-expanded image representing an item captured by an imaging device. In a first embodiment, the method comprises viewing the item with the imaging device; capturing an image of the item in a first color space, for example the original or natural color space; mapping pixel color characteristics of the image to a second color space; obtaining a color distribution of the image in the second color space; stretching or expanding the color distribution over valid values of the second color space to obtain an expanded color distribution; and using the expanded color distribution to compute new pixel characteristics in the first color space, for example to obtain a color-enhanced image. According to some embodiments of the present invention, the enhanced images may present a better color-contrast than the original images. According to some embodiments, the first color space may be the RGB color space.

In another embodiment, the step of determining a color transformation for the image may comprise mapping pixel color characteristics to a second color space; obtaining, for example estimating, a color distribution of the image in the second color space; expanding the color distribution over valid values of the second color space to obtain an expanded color distribution; and using the expanded color distribution to calculate new pixel color characteristics in the first color space. According to some embodiments, an original mean value of the color distribution may be calculated, for example based on the image, a subset of selected pixels in the image or on previous images in an image stream. According to some embodiments, a new mean value of the expanded color distribution may be determined, for example based on the image, a subset of selected pixels in the image, previous images in an image stream or on a predetermined value and new pixel color characteristics may be calculated based on the new mean value.

According to some embodiments, a second color space is not required. The received image may be captured in an original color space, and new pixel characteristics of the image may be computed in the same color space. The color distribution may also be stretched in the same color space. According to some embodiments, a color transformation that expands the range of colors of the image or a portion of the image may be determined, and a color-expanded image may be constructed using the color transformation. The colors of the image after the transformation may or may not preserve their natural (or original) hues. According to some embodiments, determining a color transformation for the image may comprise the steps of obtaining a color distribution of the image; expanding the color distribution over valid values of the color space to obtain an expanded color distribution; and using the expanded color distribution to calculate new pixel color characteristics.

In another embodiment, of the present invention, provided herein is a method of increasing color contrast of an in-vivo image captured in a gastrointestinal tract by an autonomous in vivo device, the method comprising: viewing the region of interest in the gastrointestinal tract with the autonomous in vivo device; capturing an image of the gastrointestinal tract; and constructing from the captured image a color expanded image, wherein the color expansion enhances color contrast of the image. In a further embodiment, the color expansion can be performed on a portion of an image, meaning that the method processes only part of the image, leaving the rest of it un-touched.

In a further embodiment, the invention provides a user interface with a display that provides the user with the option of viewing selected images captured by the in-vivo imaging device in either regular view or in a color enhanced view to enable more distinct viewing of the selected images.

Embodiments of the invention may provide various other benefits and/or advantages.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawings will be provided by the U.S. Patent and Trademark Office upon request and payment of the necessary fee.

The principles and operation of the system, apparatus, and method according to the present invention may be better understood with reference to the drawings, and the following description, it being understood that these drawings are given for illustrative purposes only and are not meant to be limiting, wherein.

Figure 1:
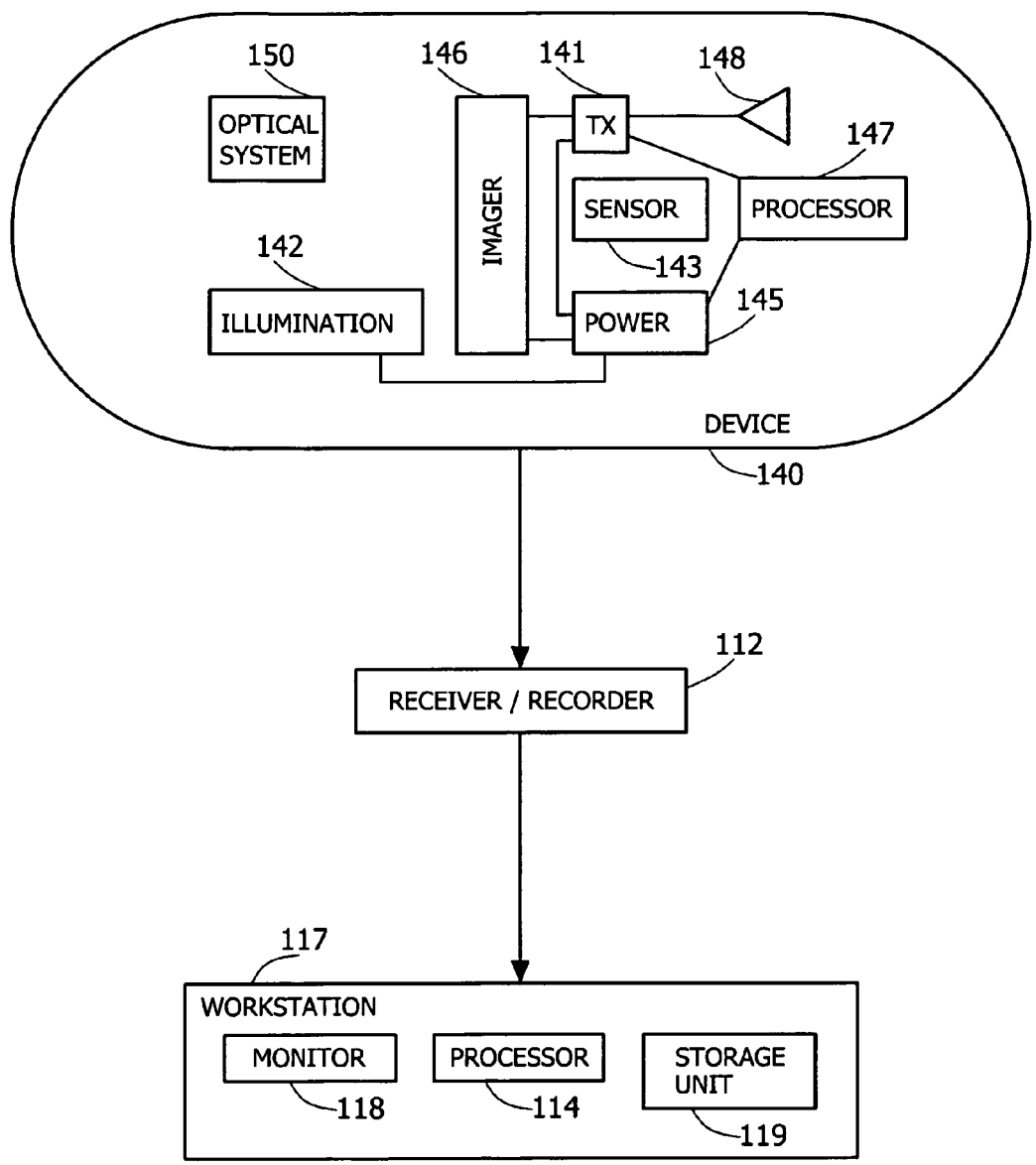
FIG. 1 is a schematic illustration of an in-vivo system according to an embodiment of the invention.
Figure 2A:
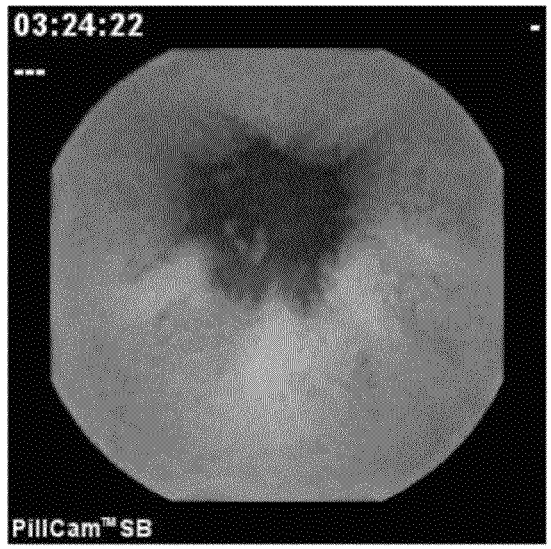
FIGS. 2A-6B show various images captured by the in-vivo imaging device in both a regular, full color view (2A, 3A, 4A, 5A and 6A) and in color-stretched view (2B, 3B, 4B, 5B and 6B)
Figure 2B:
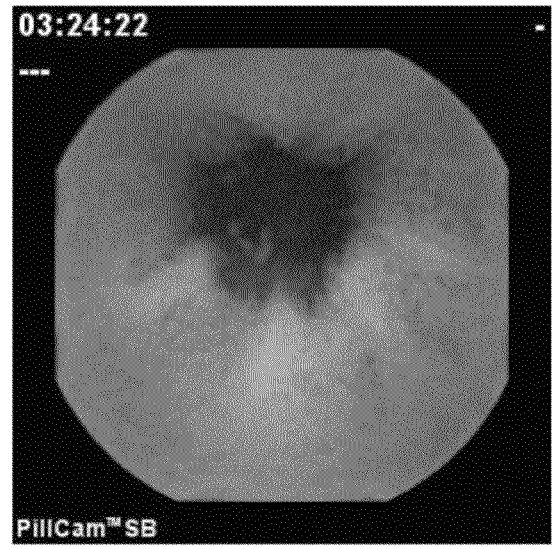
Figure 3A:
Figure 3B:
Figure 4A:
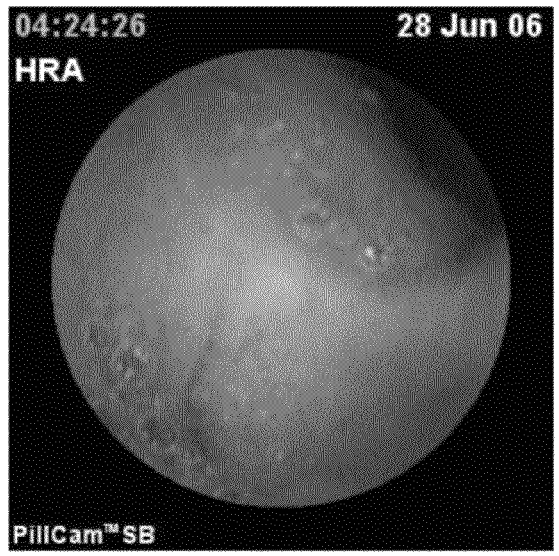
Figure 4B:
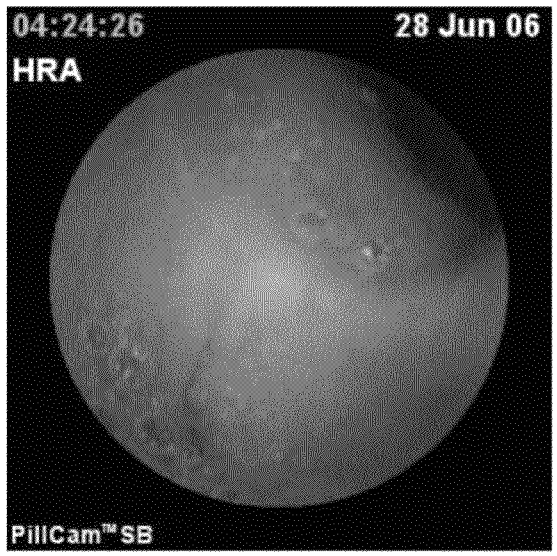
Figure 5A:
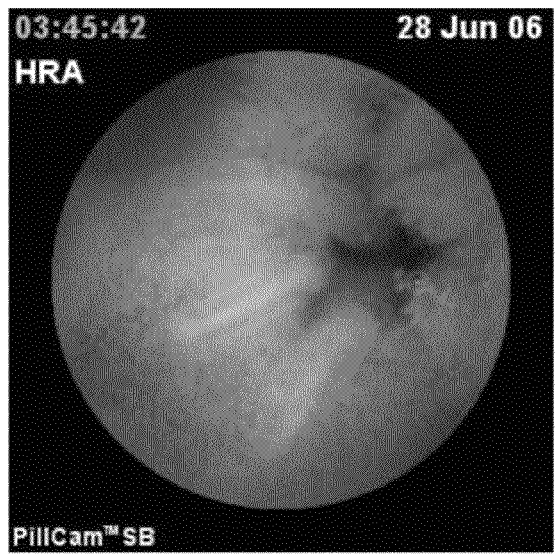
Figure 5B:
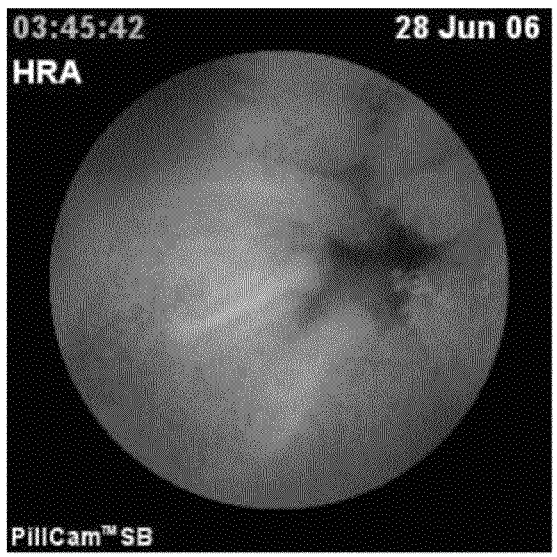
Figure 6A:
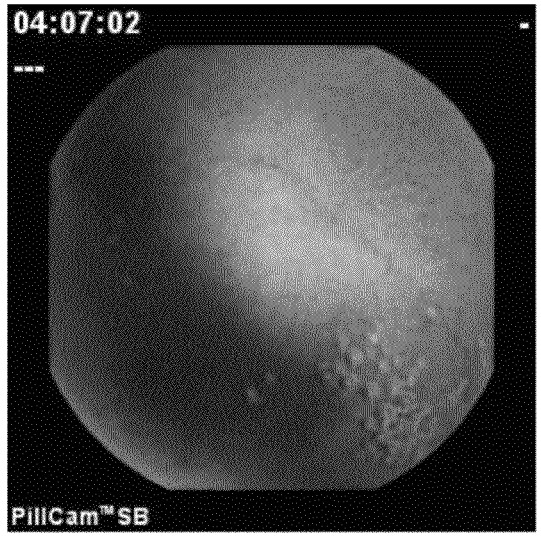
Figure 6B:
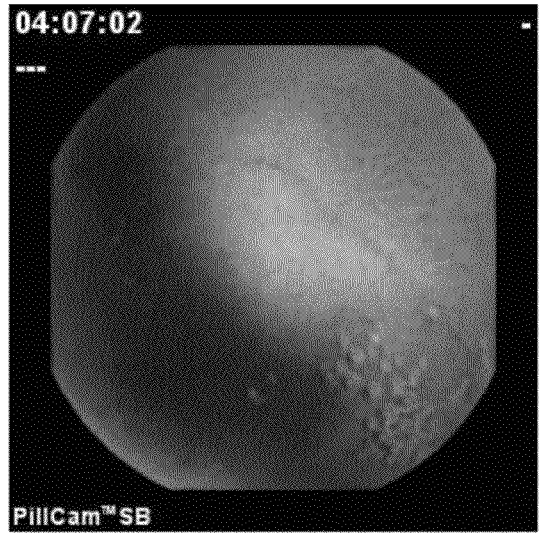

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the present invention. However, it will be understood by those skilled in the art that the present invention may be practiced without these specific details. In other instances, well-known methods, procedures, and components have not been described in detail so as not to obscure the present invention.

Some embodiments of the present invention are directed to an in-vivo device that may be inserted into a body lumen, e.g., the gastro-intestinal (GI) tract, for example, from outside the body. Some embodiments are directed to a typically one time use or partially single use detection and/or analysis device. Some embodiments are directed to a typically swallowable in-vivo device that may passively or actively progress through a body lumen, e.g., the gastro-intestinal (GI) tract, for example, pushed along by natural peristalsis. Some embodiments are directed to in-vivo sensing devices that may be passed through other body lumens, for example, through blood vessels, the reproductive tract, or the like. The in-vivo device may be, for example, a sensing device, an imaging device, a diagnostic device, a detection device, an analysis device, a therapeutic device, or a combination thereof. In some embodiments, the in-vivo device may include an image sensor or an imager and/or other suitable components. Some embodiments of the present invention may be directed to other imaging devices, not necessarily in-vivo imaging.

Devices, systems and methods according to some embodiments of the present invention, including for example in-vivo sensing devices, receiving systems and/or display systems, may be similar to embodiments described in U.S. Pat. No. 5,604,531 to Iddan et al., entitled "In-vivo Video Camera System", and/or in U.S. Pat. No. 7,009,634 to Iddan et al., entitled "Device for In-Vivo Imaging", all of which are hereby incorporated by reference in their entirety.

Devices and systems as described herein may have other configurations and/or sets of components. For example, an external receiver/recorder unit, a processor and a monitor, e.g., in a workstation, such as those described in the above publications, may be suitable for use with some embodiments of the present invention. Devices and systems as described herein may have other configurations and/or other sets of components. For example, the present invention may be practiced using an endoscope, needle, stent, catheter, etc. Some in-vivo devices may be capsule shaped, or may have other shapes, for example, a peanut shape or tubular, spherical, conical, or other suitable shapes.

Some embodiments of the present invention may include, for example, a typically swallowable in-vivo device. In other embodiments, an in-vivo device need not be swallowable and/or autonomous, and may have other shapes or configurations. Some embodiments may be used in various body lumens, for example, the GI tract, blood vessels, the urinary tract, the reproductive tract, or the like.

Embodiments of the in-vivo device are typically autonomous and are typically self-contained. For example, the in-vivo device may be or may include a capsule or other unit where all the components are substantially contained within a container, housing or shell, and where the in-vivo device does not require any wires or cables to, for example, receive power or transmit information. The in-vivo device may communicate with an external receiving and display system to provide display of data, control, or other functions. For example, power may be provided by an internal battery or an internal power source, or using a wired or wireless power-receiving system. Other embodiments may have other configurations and capabilities. For example, components may be distributed over multiple sites or units; and control information or other information may be received from an external source.

Devices, systems and methods in accordance with some embodiments of the invention may be used, for example, in conjunction with a device which may be inserted into a human body or swallowed by a person. However, embodiments of the invention are not limited in this regard, and may be used, for example, in conjunction with a device which may be inserted into, or swallowed by, a non-human body or an animal body. Other embodiments of the invention need not be used with in vivo imaging devices, and may be used for enhancing images obtained by other types of imaging devices, such as digital cameras, or virtual imaging devices.

FIG. 1 schematically illustrates an in-vivo system in accordance with some embodiments of the present invention. One or more components of the system may be used in conjunction with, or may be operatively associated with, the devices and/or components described herein or other in-vivo devices in accordance with embodiments of the invention.

In some embodiments, the system may include a device 140 having a sensor, e.g., an imager 146, one or more illumination sources 142, a power source 145, and a transmitter 141. In some embodiments, device 140 may be implemented using a swallowable capsule, but other sorts of devices or suitable implementations may be used. Outside a patient's body may be, for example, an external receiver/recorder 112 (including, or operatively associated with, for example, one or more antennas, or an antenna array), a storage unit 119 which may be or include for example one or more of a memory, a database, etc. or other storage systems, a processor 114, and a monitor 118. In some embodiments, for example, processor 114, storage unit 119 and/or monitor 118 may be implemented as a workstation 117, e.g., a computer or a computing platform.

Transmitter 141 may operate using radio waves; but in some embodiments, such as those where device 140 is or is included within an endoscope, transmitter 141 may transmit/receive data via, for example, wire, optical fiber and/or other suitable methods. Other known wireless methods of transmission may be used. Transmitter 141 may include, for example, a transmitter module or sub-unit and a receiver module or sub-unit, or an integrated transceiver or transmitter-receiver.

Device 140 typically may be or may include an autonomous swallowable capsule, but device 140 may have other shapes and need not be swallowable or autonomous. Embodiments of device 140 are typically autonomous, and are typically self-contained. For example, device 140 may be a capsule or other unit where all the components are substantially contained within a container or shell, and where device 140 does not require any wires or cables to, for example, receive power or transmit information. In some embodiments, device 140 may be autonomous and non-remote-controllable; in another embodiment, device 140 may be partially or entirely remote-controllable.

In some embodiments, device 140 may communicate with an external receiving and display system (e.g., workstation 117 or monitor 118) to provide display of data, control, or other functions. For example, power may be provided to device 140 using an internal battery, an internal power source, or a wireless system able to receive power. Other embodiments may have other configurations and capabilities. For example, components may be distributed over multiple sites or units, and control information or other information may be received from an external source.

In some embodiments, device 140 may include an in-vivo video camera, for example, imager 146, which may capture and transmit images of, for example, the GI tract while device 140 passes through the GI lumen. Other lumens and/or body cavities may be imaged and/or sensed by device 140. In some embodiments, imager 146 may include, for example, a Charge Coupled Device (CCD) camera or imager, a Complementary Metal Oxide Semiconductor (CMOS) camera or imager, a digital camera, a stills camera, a video camera, or other suitable imagers, cameras, or image acquisition components.

In some embodiments, imager 146 in device 140 may be operationally connected to transmitter 141. Transmitter 141 may transmit images to, for example, external transceiver or receiver/recorder 112 (e.g., through one or more antennas), which may send the data to processor 114 and/or to storage unit 119. Transmitter 141 may also include control capability, although control capability may be included in a separate component, e.g., processor 147. Transmitter 141 may include any suitable transmitter able to transmit image data, other sensed data, and/or other data (e.g., control data) to a receiving device. Transmitter 141 may also be capable of receiving signals/commands, for example from an external transceiver. For example, in some embodiments, transmitter 141 may include an ultra low power Radio Frequency (RF) high bandwidth transmitter, possibly provided in Chip Scale Package (CSP).

In some embodiments, transmitter 141 may transmit/receive via antenna 148. Transmitter 141 and/or another unit in device 140, e.g., a controller or processor 147, may include control capability, for example, one or more control modules, processing module, circuitry and/or functionality for controlling device 140, for controlling the operational mode or settings of device 140, and/or for performing control operations or processing operations within device 140. According to some embodiments, transmitter 141 may include a receiver which may receive signals (e.g., from outside the patient's body), for example, through antenna 148 or through a different antenna or receiving element. According to some embodiments, signals or data may be received by a separate receiving device in device 140.

Power source 145 may include one or more batteries or power cells. For example, power source 145 may include silver oxide batteries, lithium batteries, other suitable electrochemical cells having a high energy density, or the like. Other suitable power sources may be used. For example, power source 145 may receive power or energy from an external power source (e.g., an electromagnetic field generator), which may be used to transmit power or energy to in-vivo device 140.

In some embodiments, power source 145 may be internal to device 140, and/or may not require coupling to an external power source, e.g., to receive power. Power source 145 may provide power to one or more components of device 140 continuously, substantially continuously, or in a non-discrete manner or timing, or in a periodic manner, an intermittent manner, or an otherwise non-continuous manner. In some embodiments, power source 145 may provide power to one or more components of device 140, for example, not necessarily upon-demand, or not necessarily upon a triggering event or an external activation or external excitement.

Optionally, in some embodiments, transmitter 141 may include a processing unit or processor or controller, for example, to process signals and/or data generated by imager 146. In another embodiment, the processing unit may be implemented using a separate component within device 140, e.g., controller or processor 147, or may be implemented as an integral part of imager 146, transmitter 141, or another component, or may not be needed. The processing unit may include, for example, a Central Processing Unit (CPU), a Digital Signal Processor (DSP), a microprocessor, a controller, a chip, a microchip, a controller, circuitry, an Integrated Circuit (IC), an Application-Specific Integrated Circuit (ASIC), or any other suitable multi-purpose or specific processor, controller, circuitry or circuit. In some embodiments, for example, the processing unit or controller may be embedded in or integrated with transmitter 141, and may be implemented, for example, using an ASIC.

Processor 114 may include a processing unit, processor or controller. The processing unit may include, for example, a CPU, a DSP, a microprocessor, a controller, a chip, a microchip, a controller, circuitry, an IC, an ASIC, or any other suitable multi-purpose or specific processor, controller, circuitry or circuit.

In some embodiments, imager 146 may acquire in-vivo images continuously, substantially continuously, or in a non-discrete manner, for example, not necessarily upon-demand, or not necessarily upon a triggering event or an external activation or external excitement; or in a periodic manner, an intermittent manner, or an otherwise non-continuous manner.

In some embodiments, transmitter 141 may transmit image data continuously, or substantially continuously, for example, not necessarily upon-demand, or not necessarily upon a triggering event or an external activation or external excitement; or in a periodic manner, an intermittent manner, or an otherwise non-continuous manner.

In some embodiments, device 140 may include one or more illumination sources 142, for example one or more Light Emitting Diodes (LEDs), "white LEDs", or other suitable light sources. Illumination sources 142 may, for example, illuminate a body lumen or cavity being imaged and/or sensed. An optional optical system 150, including, for example, one or more optical elements, such as one or more lenses or composite lens assemblies, one or more suitable optical filters, or any other suitable optical elements, may optionally be included in device 140 and may aid in focusing reflected light onto imager 146, focusing illuminated light, and/or performing other light processing operations.

In some embodiments, device 140 may include one or more illumination sources 142 wherein the illumination sources are in a color transmission range that is narrower than "white LEDs" and may be red, yellow, blue, green, purple or orange in certain embodiments. In certain embodiments, the color of the illumination source is selected based on the pathology sought to be detected, using the methods described herein. In certain embodiments, narrowing the wavelength emitted by the illumination source 142 may assist in obtaining a better contrast using the methods described herein. Accordingly and in another embodiment, device 140 comprises an illumination source 142 wherein the illumination source is one or more light emitting diodes, emitting light at a wavelength of between about 430 and 530 nm (Blue LED) with a peak at about 480 nm, or in another embodiment a green LED emitting light at a wavelength of between about 480 and 580 nm, with a peak at about 530 nm, or in another embodiment a red LED emitting light at a wavelength of between about 580 and 680 nm, with a peak at about 630 nm.

In some embodiments, illumination source(s) 142 may illuminate continuously, or substantially continuously, for example, not necessarily upon-demand, or not necessarily upon a triggering event or an external activation or external excitement. In some embodiments, for example, illumination source(s) 142 may illuminate a pre-defined number of times per second (e.g., two, three or four times), and operate in such a way substantially continuously, e.g., for a time period of two hours, four hours, eight hours, or the like; or in a periodic manner, an intermittent manner, or an otherwise non-continuous manner.

In some embodiments, the components of device 140 may be enclosed within a housing or shell, e.g., capsule-shaped, oval, or having other suitable shapes. The housing or shell may be substantially transparent or semi-transparent, and/or may include one or more portions, windows or domes that may be substantially transparent or semi-transparent. For example, one or more illumination source(s) 142 within device 140 may illuminate a body lumen through a transparent or semi-transparent portion, window or dome; and light reflected from the body lumen may enter the device 140, for example, through the same transparent or semi-transparent portion, window or dome, or, optionally, through another transparent or semi-transparent portion, window or dome, and may be received by optical system 150 and/or imager 146. In some embodiments, for example, optical system 150 and/or imager 146 may receive light, reflected from a body lumen, through the same window or dome through which illumination source(s) 142 illuminate the body lumen.

Data processor 114 may analyze the data received via external receiver/recorder 112 from device 140, and may be in communication with storage unit 119, e.g., transferring frame data to and from storage unit 119. Data processor 114 may provide the analyzed data to monitor 118, where a user (e.g., a physician) may view or otherwise use the data. In some embodiments, data processor 114 may be configured for real time processing and/or for post processing to be performed and/or viewed at a later time. In the case that control capability (e.g., delay, timing, etc) is external to device 140, a suitable external device (such as, for example, data processor 114 or external receiver/recorder 112 having a transmitter or transceiver) may transmit one or more control signals to device 140.

Monitor 118 may include, for example, one or more screens, monitors, or suitable display units. Monitor 118, for example, may display one or more images or a stream of images captured and/or transmitted by device 140, e.g., images of the GI tract or of other imaged body lumen or cavity. Additionally or alternatively, monitor 118 may display, for example, control data, location or position data (e.g., data describing or indicating the location or the relative location of device 140), orientation data, and various other suitable data. In some embodiments, for example, both an image and its position (e.g., relative to the body lumen being imaged) or location may be presented using monitor 118 and/or may be stored using storage unit 119. Other systems and methods of storing and/or displaying collected image data and/or other data may be used.

In one example, a physician or a health care specialist may receive a stream of in vivo images, for example captured by a swallowable capsule or by another in vivo imaging device, such as an endoscope. The physician may need to carefully review the image stream, for example to determine if there are any abnormalities or pathologies which may be identified in the images. An abnormality viewed in an image captured by a capsule without color contrast enhancement, may be very similar in color to the healthy tissue around it. Therefore it may be difficult to distinguish between a healthy segment of the tissue to an abnormal segment or a pathology such as a tumor or a lesion. In addition, the amount of images captured by the imaging device and presented to the physician may be very large. An image stream captured by swallowable capsule may comprise thousands of images, for example the imaging procedure may take for example 8 hours in a constant or variable frame rate of for example 2-36 frames per second. The imaging procedure may take more or less time, for example depending on the patient or on the type of procedure performed. In some examples, an adaptive frame rate of image capture may be used, for example taking one frame every 2 minutes when the capsule is not moving or when it is moving extremely slowly, and when the capsule is moving fast the imaging rate may increase for example up to 36 frames per second. In some embodiments, the frame rate may be lower than $1/120$ frames per second, or higher than 36 frames per second. Therefore an image stream containing thousands of images, for example 50,000 images, may be obtained. Abnormalities in the gastrointestinal tract, such as abnormal tissue segments, tumors or other pathologies, may appear in only a few images of the stream.

In one example, the color variation of the abnormality compared to the healthy tissue may be very slight—for example the color of the diseased tissue may be slightly more reddish than the healthy tissue. In another example, only the color of the area around the diseased tissue may have a bit darker or a bit lighter color than the healthy tissue. The color of the diseased tissue may also be different than red, for example more whitish or more bluish. Therefore it may be useful to highlight or otherwise indicate the difference for the physician between the colors of the abnormalities in comparison to the colors of the surrounding healthy tissue (for example by enhancing the color contrast of the images including the pathology as may be enabled by embodiments of the present invention). Such indication may allow a faster review of the image stream without missing or overlooking a suspected pathology area, and thereby may enable shortening the time that the physician spends reviewing the images.

Typically, device 140 may transmit image information in discrete portions. Each portion may typically correspond to an image or a frame; other suitable transmission methods may be used. For example, in some embodiments, device 140 may capture and/or acquire an image once every half second, and may transmit the image data to external receiver/recorder 112. Other constant and/or variable capture rates and/or transmission rates may be used.

Identifying pathologies such as tumors, lesions or ulcers and the like within images of the GI tract may be complicated by the fact that the gastrointestinal tract and the item or pathology sought to be viewed have very similar background color. The color of a tumor for example may be very similar to the healthy tissue around it, however a trained physician may be able to distinguish between the healthy tissue and the tumor, based for example on slight difference in the color which may be difficult to distinguish for the untrained eye. Abnormalities may also be distinguished in other methods, for example based on difference in shape from the normal tissue, or based on difference of texture in a healthy tissue compared to a diseased tissue. According to embodiments of the present invention, the colors of the original image may be expanded and changed, for example to different shades and unnatural colors, in order to provide a better contrast between healthy tissue and diseased tissue.

Accordingly, provided herein is a computer-implemented method for constructing a color expanded image, for example an image representing an item viewed by an autonomous in vivo device. In one embodiment of the invention, the color contrast of the image is enhanced by transforming the values of the original color space, for example the natural color space and expanding it in such a way that the item observed will have a higher color contrast, and in a preferred embodiment the item may have the highest color contrast possible in the available color values.

In one embodiment of this method, the item may be viewed with the autonomous in vivo device, and an image is captured. Pixel characteristics of the image are mapped into a another color space. A color contrast enhancement of the image is induced with a color transformation that expands the color distribution.

FIGS. 2A, 3A, 4A, 5A and 6A show various images that were captured in vivo. As can be seen in these figures (best viewed in color), the images have a reddish tint, which is due to the fact that the gastrointestinal tract itself in fact has a reddish color. It may be somewhat difficult to view pathologies such as tumors, lesions or ulcers and the like, with as much detail and clarity as would be desired, due to the fact that the pathologies have the same reddish tint that the gastrointestinal tract has.

FIGS. 2B, 3B, 4B, 5B and 6B show the images after having been color-enhanced in accordance with an embodiment of the invention. As can be seen in these figures (best viewed in color), the color-contrast of the images has been enhanced to provide a better color-contrast within the images, such that pathologies such as tumors, lesions or ulcers and the like, may be viewed with more detail and clarity. According to one embodiment, the enhanced colors are artificial colors, which may not represent the natural colors of the item sought to be viewed, and the borders of the item may be emphasized as a result of the color enhancement.

In another embodiment, use of the color transformation in the methods decribed herein comprises performing the following operations: obtaining the pixel color characteristics of the image (See FIG. 7A); transforming the original pixel color characteristics to a different color coordinate set (according to one embodiment this step may be optional); determining the mean value of the original color distribution; and correcting the pixel color characteristics based on a new mean and a scaling factor. According to some embodiments, the mean of the predetermined color coordinates may be computed or set for a given predetermined color wavelength range. The mean value of the original color distribution may be determined based on an image, or a portion of an image. According to some embodiments, the mean may be calculated based on a series of sequential images or on portions of the sequential images. For example, only a portion of the image, such as a circle which is centered in the center of the image, may be used for calculating the mean.

In another embodiment, use of the color transformation in the methods decribed herein comprises performing the following operations: obtaining the pixel color characteristics of the image; determining a new mean value of the original color distribution using a normalized RGB color space (r, g, b); and correcting the pixel color characteristics based on the new mean.

A color is a visual sensation produced by a specific spectral power distribution incident on the retina. In one embodiment, characterizing the pixel characteristic of the images captured involves calculating color response functions using a color coordinate systems referred to in another embodiment as color spaces or spectral spaces, which are means by which colors can be specified, created and visualized. Different color spaces are better for different applications. In one embodiment, the methods described herein utilize color management systems (CMSs) to characterize the captured images and to transform color data between the color imaging systems.

A multi-spectral image is a collection of two or more monochrome images of the same scene. Multi-spectral images can be described in any one of a plurality of known spectral or color spaces. For example, one well-known multi-spectral image is an RGB (red-green-blue) color image. An RGB color image consists of a red, a green and a blue component and, thus, the image is said to be described in RGB spectral space. In one embodiment, the original color coordinate system used is RGB.

As also described herein, the matrix of digital data values obtained using the methods described herein is generally referred to as a "digital image" or more simply an "image" and may be stored in a digital data storage device, such as a memory, for example, as an array of numbers representing the spatial distribution of energy at different wavelengths in a scene. Digital multi-spectral images, as well as all digital images, are represented by an array of pixels. Each of the numbers in the array corresponds to a digital value typically referred to as a "picture element" or a "pixel" or as "image data." Thus, in one embodiment, a pixel represents a single sample which is located at specific spatial coordinates in the image.

For example, using the so-called RGB color scheme in which a color and luminance value for each pixel can be computed from the RGB values, reference is sometimes made herein to each pixel being represented by a predetermined number of bits (e.g., eight bits) which represent the color red (R bits), a predetermined number of bits (e.g., eight bits) which represent the color green (G bits) and a predetermined number of bits (e.g., eight bits) which represent the color blue (B-bits). Thus, in an eight bit color RGB representation, a pixel may be represented by a twenty-four bit sequence. It is of course possible to use greater or fewer than eight bits for each of the RGB values.

In another embodiment, the color space that is used is Commission Internationale de l'Eclairage L*a*b* (CIELAB) color space. The CIE has defined a system that classifies color according to the HVS (the human visual system). Using this system, any color can be specified in terms of its CIE coordinates.

In another embodiment, color pixels are represented using other color or spectral schemes such as a hue, saturation, brightness (HSB) scheme or a cyan, magenta, yellow, black (CMYK) scheme. In certain embodiments, the schemes used in the methods described herein are RGB, CMY (cyan, magenta, yellow), CYMK, HSI (intensity), HCI (chroma/colorfulness), TSD (hue saturation and darkness), HSV (value), or YCbCr, YUV, UVW, U'V'W', YCC and YIQ (television transmission colour spaces) coordinate set or color schemes, as well as CIE L*u*v* and CCIR (Comite Consultatif International des Radiocommunications) 601 YCbCr, spectral spaces. It should thus be noted that the techniques described herein are applicable to a plurality of color schemes including but not limited to the above mentioned RGB, HSB, CMYK schemes as well as the Luminosity and color axes a & b (Lab) color coordinate system, the Karhunen-Loeve color coordinate system, the retinal cone color coordinate system and the CIE X,Y,Z scheme.

In one embodiment, once the image, i.e., the pixel color characteristics in, for example, RGB format, is obtained, the original pixel color characteristics are transformed to a different color coordinate set, or alternatively the original coordinate set is normalized and r=R/(R+G+B) and g=G/(R+G+B) are evaluated.

In another embodiment, the mean of a portion of the image, for example the lighted area of the image in the u' v' coordinates, is then evaluated. According to one embodiment, the mean value of the color distribution may be determined for a given predetermined color wavelength range.

In one embodiment, a new mean is determined for an expanded color distribution. After determining the new mean, the next step is transforming the pixel color characteristics based on the new mean, which comprises assigning a new u' v' coordinate value, whereby the new coordinate value is the sum of [the product of (the difference between the original coordinate value and the mean value of the original color distribution in the u' v' color space) and a scaling factor] and the coordinate value of the new mean, as follows:

$$\text{New\_}u' = (u' - \bar{u}) \cdot \text{ScaleFactor} + \overline{\text{New\_}u}$$

$$\text{New\_}v' = (v' - \bar{v}) \cdot \text{ScaleFactor} + \overline{\text{New\_}v}$$

wherein $\bar{u}$ and $\bar{v}$ denote the original mean values in the u' v' color space;
$\overline{\text{New\_}u}$ and $\overline{\text{New\_}v}$ denote the new mean values in the u' v' color space;
New_u' and New_v' denote the new pixel coordinates in the u' v' color space;
u' and v' denote the original pixel coordinates in the u' v' color space;
and ScaleFactor denotes the selected scaling factor.

In a first embodiment, this original mean value is evaluated for each frame separately. In another embodiment, this mean is evaluated in advance based on statistics of many GI images. In another embodiment the calculation of the original mean value can be based on IIR, for example taking into account history values calculated in recent or previous images in the stream.

In one embodiment, the scaling or expansion factor used in the methods described herein is variable and may be selected as a function based on an image region. An "image region" or more simply a "region" is a portion of an image. For example, if an image is provided as a 32×32 pixel array, a region may correspond to a 4×4 portion of the 32×32 pixel array. In a preferred embodiment, the pixel array is much larger, for example using an imager that is 256×256 pixels. In another embodiment, the scaling factor is constant gain (for example, 2.5). In yet another embodiment, the scaling factor may be selected or fine-tuned based on input from the user. Input from the user may be used for determining other parameters, for example the new mean value of the expanded color distribution. The scale factor may be changed as a function of other parameters, such as luminance (Y). For example, if the luminance is low, the scale factor may be lower than the user's selected input in order to avoid adding unnecessary noise in the image. In one embodiment, a predetermined region, or area of interest (AOI), is determined using an alternative spectroscopic method, such as ultrasound in one embodiment. Accordingly, and in certain embodiment, the pixel array is adapted to yield the preferred color contrast of the area of interest, while outside the AOI, the color contrast of the pixel array may be lower, higher, and may remain unchanged.

In one embodiment, $\overline{New\_u}$ and $\overline{New\_v}$ refer to preselected values in the u' v' color space, selected as the desired mean based on which the color transformation is to be performed. According to one embodiment, the mean of the color distribution may be shifted to a central area in the second color space and then the color distribution may be stretched, to utilize a larger color range. According to one embodiment, the $\overline{New\_u}$ and $\overline{New\_v}$ new mean values may be selected in a central position of the second color space, in order to enable maximal expansion in all directions of the color characteristics, thereby enabling a higher or maximal color contrast of the enhanced image. According to another embodiment, the new mean values need not be selected in a central position, and the expansion of the color characteristics may be performed in a non-symetrical manner around the selected new mean values.

The calculation/selection of the new mean and values may depend on the image region of interest in one embodiment, or the pathology, item, region and the like in other embodiments. For example, $\overline{New\_u}$ and $\overline{New\_v}$ in one embodiment might be white for better visualization and separation, and in another embodiment might be the original mean of image to keep natural or original colors. Thus, for white: $\overline{New\_u}$ and $\overline{New\_v}$ are 0.1978, 0.4683. For normalized r, g, the white point is 0.333, 0.333. In a preferred embodiment, in images that are substantially reddish, for example in vivo images, the mean may be placed in the gray or white area of the second color space, for example the u', v' color space.

In one embodiment, New_u' and New_v' are then transformed back from u' v' image values to RGB image values. Normalized r, g, b space may be used instead of the u' v' space. Included in this step is preferably correcting non plausible data. For example, correcting non plausible data may be performed by cropping negative coordinate values and coordinate values larger than 1. In other embodiments, values that are not in the valid range or a predetermined range, for example 0-255, may be cropped or corrected to a predetermined valid value.

In this step, the third component is preferably kept constant. For example, in u' v', Y (luminance) is kept constant. Also, in r g, the sum of R, G, B may be kept constant. In addition, max (R, G, B) may also be kept fixed, instead of the sum of R, G, B.

The skilled practitioner will readily appreciate that new pixel color values (coordinates) in the second color space may be changed until the image or the image region sought to be viewed yields the optimal color contrast. Using software, the user may be able to control, for example manually refine, the color contrast. Alternatively, the color contrast value may be changed as a function of the luminance, i.e., decrease the color contrast in low values of luminance in order to avoid emphasizing color noise in low intensities. In one embodiment, the values of u and v are changed so that the resulting image yields an image utilizing for example the full spectrum of visible light to provide better color contrast compared to the red-tinted images of the lumen. In certain embodiments, optimal contrast is obtained by varying the values of $\overline{New\_u}$ and $\overline{New\_v}$ by the user. In one embodiment, the wavelength of the illumination source 142 is adjusted to provide optimal contrast between a pathology and a background pattern associated with the pathology. As described herein, in certain embodiments, providing optimal color contrast refers to providing maximum color contrast between an observed pathology and a background pattern associated with the pathology. In another embodiment, the wavelength of the illumination source 142 is adjusted to provide optimal color contrast between a healthy structure and a corresponding pathology. In one embodiment, optimal color contrast, as described herein, refers to varying the values of $\overline{u}$ and $\overline{v}$ in such a way as to compensate for low luminescence intensity in one embodiment, or high luminescence intensity in another embodiment.

According to one embodiment, the expansion of the color values may be calculated without determining a new mean value.

Similarly, and in another embodiment, the color coordinate system used to transform the data to and from, may be changed to optimize the observed image region or pathology viewed. In one embodiment, the methods described hereinabove are used for methods of enhancing color contrast in an image region described herein.

Figure 8:
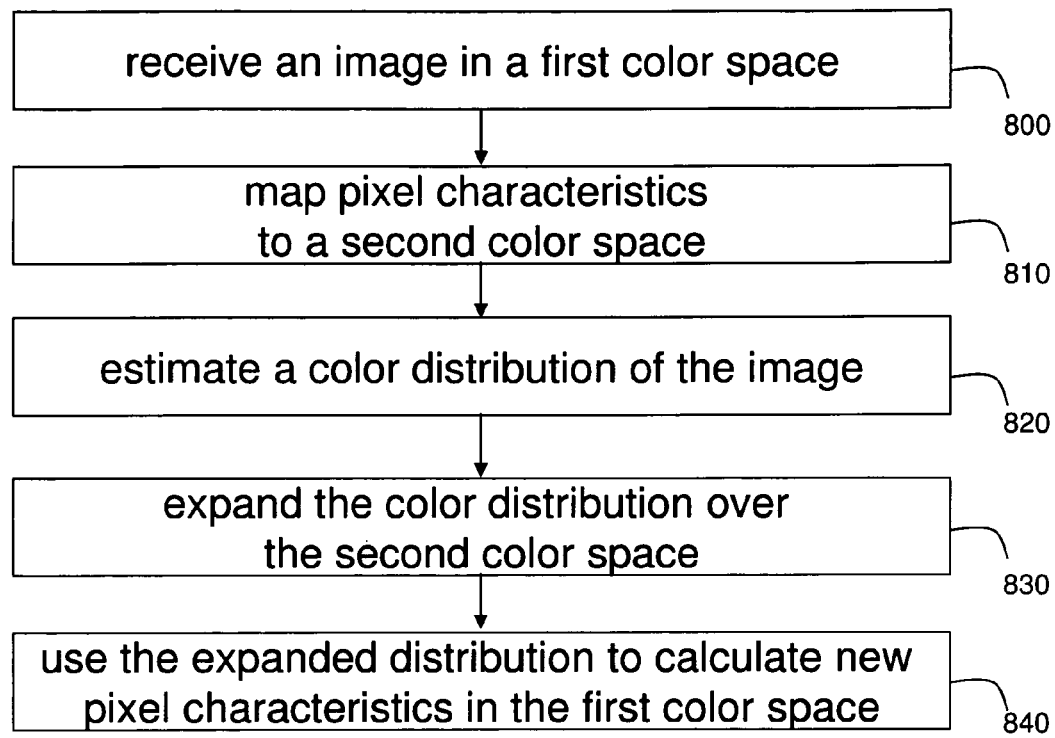
FIG. 8 is a schematic block diagram illustrating a method according to an embodiment of the invention.

Reference is now made to FIG. 8. Accordingly, and in one embodiment, provided herein is a method of increasing color contrast of an image or a portion of an image, the method comprising: receiving or obtaining images and from the received images, constructing a color expanded image, wherein the color expansion enhances color contrast of the image or of a region of interest within an image.

In another embodiment, constructing a color expanded image for increasing color contrast of an image or a portion of an image in a gastrointestinal tract viewed by an autonomous in vivo device comprises the steps of: receiving an image in a first color space (800); mapping pixel characteristics, such as brightness and color values in certain embodiments of the image to a second color space (810) and estimating a color distribution of the image (820); expanding the color distribution over valid values of the second color space (830) to obtain a stretched/expanded distribution, and using the expanded color distribution to compute new pixel characteristics in the first color space (840). According to one embodiment, computing new pixel characteristics may comprise inducing a color transformation to the pixel characteristics based on the stretched distribution. In one embodiment, constructing the color-expanded image comprises the operations of obtaining the pixel color characteristics; transforming the original pixel color characteristics to a different color coordinate set; for a given predetermined color wavelength range, determining a new mean value of the expanded color distribution; and determining the pixel color characteristics based on the new mean.

In one embodiment, the coordinate set used, or the new mean values or scaling factors in other embodiments are selected based on the pathologies sought to be imaged.

In some embodiments, the image analysis and/or comparison may be performed in substantially real time, for example, while device 140 is in-vivo, while imager 146 acquires images, while transmitter 141 transmits image data, while receiver/recorder 112 receives image data, and/or while workstation 117 displays in-vivo images.

In another embodiment, the invention provides a graphical user interface, which may be displayed on monitor 118, that provides the user with the option of viewing a selected image captured by the in-vivo imaging device in either regular view or in the color expanded or "enhanced" color view, e.g., in the full spectrum of visible colors. This interface allows the user to enable more distinct viewing of the selected images at will. In one embodiment, the enhanced color contrast view may be applied to selected images only, for example images selected by the physician or images automatically selected by a processing unit such as processing unit 114 shown in FIG. 1. These images may be suspected of showing a pathology or an abnormality of the gastrointestinal tissue. In another embodiment, the enhanced color view may be applied to all images in the image stream, or to some images, for example every second or third image, or every $100^{th}$ image. Other configurations of applying the enhanced color view may be used.

According to one embodiment, the level of color contrast enhancement may be determined by a user, for example while viewing the image stream. In one example, the user may set the level of color contrast enhancement by selecting a level from a list of predetermined levels, or by moving a sliding button across a color contrast enhancement level bar, which for example may gradually change the setting of the color contrast enhancement. Other user interface implementations may be used. In one embodiment, the enhanced image output of the contrast enhancement may be closer to the natural colors of the tissue when the level is set to a lower contrast level, and may be very different from the natural colors of the tissue (as originally images by the imager) when the level of color contrast enhancement is set to a higher level.

The following example is presented in order to more fully illustrate the preferred embodiments of the invention. It should in no way be construed, however, as limiting the broad scope of the invention.

EXAMPLES

Example 1

Method for Generating Blue Enhanced Gastrointestinal Image

The following is an example of the color expansion used in one embodiment of original and converted color coordinate sets.

In this example, the RGB images were obtained, as shown in FIGS. 2A, 3A, 4A, 5A and 6A. The RGB values were then transformed to a second set of coordinates (u' v' color space).

RGB to u'v':
To transform from RGB to XYZ (with D65 white point), the transformation matrix is as follows:

$$\begin{bmatrix} X \\ Y \\ Z \end{bmatrix} = \begin{bmatrix} 0.412453 & 0.357580 & 0.180423 \\ 0.212671 & 0.715160 & 0.072169 \\ 0.019334 & 0.119193 & 0.950227 \end{bmatrix} * \begin{bmatrix} R \\ G \\ B \end{bmatrix}$$

A white point is a set of chromaticity coordinates that serves to define the color "white" in an image. D65 indicates 6500 degrees Kelvin.

XYZ to u' v'=

$u'=4X/(X+15Y+3Z)$ $v'=9Y/(X+15Y+3Z)$

The new coordinate values were then expanded using the color-expansion function presented herein:

$New\_u'=(u'-\bar{u}) \cdot ScaleFactor+\overline{New\_u}$ $New\_v'=(v'-\bar{v}) \cdot ScaleFactor+\overline{New\_v}$ The expanded coordinate values were then transformed back from u'v' color space (or normalized r, g) to RGB color space. As stated above, the third component Y (luminance) is kept constant.

u'v' to RGB:

u' v'→XYZ=

$X=9/4*Y*u'/v'$

Y (remains unchanged)

$Z=((4*X/u')-X-15*Y)/3;$

To transform from XYZ to RGB (with D65 white point), the matrix transform used is:

$$\begin{bmatrix} R \\ G \\ B \end{bmatrix} = \begin{bmatrix} 3.240479 & -1.537150 & -0.498535 \\ -0.969256 & 1.875992 & 0.041556 \\ 0.055648 & -0.204043 & 1.057311 \end{bmatrix} * \begin{bmatrix} X \\ Y \\ Z \end{bmatrix}$$

The images are displayed with the enhanced color. See FIGS. 2B, 3B, 4B, 5B and 6B, as compared to the original images in FIGS. 2A, 3A, 4A, 5A and 6A.

In another embodiment, fixed gain on G and B channels (for example, 1.5 on G and 3 on B) may be applied, however pathologies for example in in-vivo images may be less noticeable. In this embodiment the R, G, B values may be corrected (for example, the values may be cropped or divided by a single predetermined or computed factor) in order to remain in the range of valid values. The R channel may be kept constant, since it may use a wide dynamic range in certain configurations such as in vivo images. In other embodiments, the gain on R, G and B channels may be calculated and expanded according to specific pixel characteristics. In such embodiments, a second color space need not be used, and all calculations may be performed on the original color space.

Figure 7A:
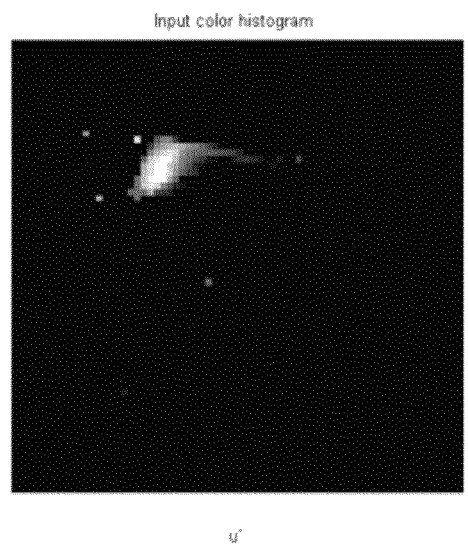
FIG. 7A shows a histogram of color coordinates of a subset of pixels of the images captured by the in-vivo imaging device.
Figure 7B:
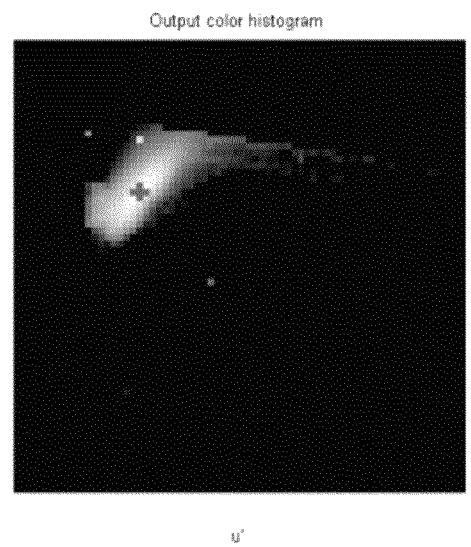
FIG. 7B shows a histogram of color coordinates of a subset of image pixels after color stretching using the methods of the invention.

Based on 115 frames samples from an in-vivo gastro-intestinal test case (67 frames from stomach, 16 from SB, 32 from colon), a histogram of u' v' coordinates of a subset of pixels in the images was prepared before and after the color transformation in u'v' dimension. For example, the subset of pixels may include all lighted pixels, or may include a group of pixel which matches a selection condition or criterion, for example a predetermined condition. FIG. 7A shows the histogram of u' v' coordinates of the subset of pixels which includes all pixels in a lighted area of the images captured by the in-vivo imaging device, and FIG. 7B shows the histogram of u' v' coordinates of all pixels in a lighted area of the images after color expansion using the methods of the invention. The histogram is very sharp, so its logarithm was plotted, normalized by the maximum. Pure colors are also plotted for reference, and the white point, which may be used as the new mean according to a preferred embodiment, is described by the "+" sign.

The processes presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems appears from the description herein. In addition, embodiments of the present invention are not described with reference to any particular programming language. It will be appreciated that a variety of programming languages may be used to implement the teachings of the invention as described herein.

Unless specifically stated otherwise, as apparent from the discussions herein, it is appreciated that throughout the specification discussions utilizing terms such as "estimating", "processing", "computing", "calculating", "determining", or the like, typically refer to the action and/or processes of a computer or computing system, or similar electronic computing device (e.g., a "computer on a chip" or ASIC), that manipulate and/or transform data represented as physical, such as electronic, quantities within the computing system's registers and/or memories into other data similarly represented as physical quantities within the computing system's memories, registers or other such information storage, transmission or display devices.

It will be appreciated by persons skilled in the art that the present invention is not limited to what has been particularly shown and described hereinabove.

Having described preferred embodiments of the invention with reference to the accompanying drawings, it is to be understood that the invention is not limited to the precise embodiments shown and described hereinabove. Rather, various changes and modifications may be effected therein by those skilled in the art without departing from the scope or spirit of the invention, and the scope of the present invention is defined only by the claims, which follow.

What is claimed is:

1. A computer-implemented method of increasing contrast of an image, the method comprising:
  receiving, by a processor, the image in a first color space;
  determining, by the processor, a color transformation for the image by:
    mapping pixel color characteristics to a second color space,
    estimating a color distribution of the image in the second color space,
    expanding the color distribution in the second color space to obtain an expanded color distribution, and
    using the expanded color distribution to calculate new pixel color characteristics in the first color space; and
  the processor using the color transformation to construct a color-expanded image, wherein the color transformation expands the range of colors of at least a portion of the image.

2. A computer implemented method of increasing contrast of an image, the method comprising:
  receiving, by a processor, the image in a first color space;
  determining, by a processor, a color transformation for the image, comprising:
    estimating a color distribution of the image;
    expanding the color distribution over valid values of the color space to obtain an expanded color distribution; and
    using the expanded color distribution to calculate new pixel color characteristics; and
  the processor using the color transformation to construct a color-expanded image, wherein the color transformation expands the range of colors of at least a portion of the image.

3. The method of claim 1, further comprising:
  determining an original mean value of the color distribution; and
  determining a new mean value of the expanded color distribution;
  and wherein the new pixel color characteristics are calculated based on the new mean value.

4. The method of claim 3, wherein the new mean value is determined based on at least: the image, a subset of selected pixels in the image, previous images in an image stream or a predetermined value.

5. The method of claim 3, wherein the original mean value is determined based on at least: the image, a subset of selected pixels in the image, or previous images in an image stream.

6. The method of claim 3, wherein the first color space is an RGB color space.

7. The method of claim 6, whereby the second color space is normalized rgb, CYM, CYMK, HIS, HSV, YCbCr, YUV, UVW, U'V'W', CIE or YIQ color space.

8. The method of claim 3, wherein the new pixel color characteristics are calculated in the second color space with the following equation, and then transformed back to the first color space:

$$\text{New\_}u' = (u' - \bar{u}) \cdot \text{ScaleFactor} + \overline{\text{New\_}u}$$

$$\text{New\_}v' = (v' - \bar{v}) \cdot \text{ScaleFactor} + \overline{\text{New\_}v}$$

wherein
  $\bar{u}$ and $\bar{v}$ denote the original mean values in the second color space;
  $\overline{\text{New\_}u}$ and $\overline{\text{New\_}v}$ denote the new mean values in the second color space;
  New_u' and New_v' denote the new pixel color characteristics in the second color space;
  u' and v' denote the original pixel color characteristics in the second color space; and
  ScaleFactor denotes a selected scaling factor; and
  wherein a luminance value is kept constant.

9. The method of claim 8 wherein the scaling factor is selected based on user input.

10. The method of claim 1, further comprising correcting non plausible pixel color characteristics.

11. The method of claim 3, whereby the new mean is selected based on: a given characteristic of an area of interest, a predetermined value or user input.

12. The method of claim 11, whereby the given characteristic of the area of interest is a pathology.

13. The method of claim 1, wherein the image is an in-vivo image.

14. The method of claim 13, wherein the image is captured by a swallowable capsule.

* * * * *